United States Patent [19]

Holmes

[11] 4,026,666

[45] May 31, 1977

[54] METHOD OF DETERMINING SOY MATERIAL IN FOODS

[75] Inventor: Leo G. Holmes, Natick, Mass.

[73] Assignee: The United States of America as represented by the Secretary of the Army, Washington, D.C.

[22] Filed: May 10, 1976

[21] Appl. No.: 685,018

[52] U.S. Cl. .............................. 23/230 M; 23/230 R
[51] Int. Cl.$^2$ .................. G01N 33/02; G01N 21/34
[58] Field of Search ........ 23/230 R, 230 B, 230 M; 252/408

[56] References Cited

UNITED STATES PATENTS 3,563,708  2/1971  Stone et al. .......................... 23/230
3,892,530  7/1975  Felix et al. ....................... 23/230 M Primary Examiner—R.E. Serwin
Attorney, Agent, or Firm—Nathan Edelberg; Robert P. Gibson; Charles C. Rainey

[57] ABSTRACT

A method of determining the amount of soy material in a food product by determining the fluorescence intensity at a wavelength of about 445 nanometers produced by excitation at a wavelength of 360 nanometers in the ultraviolet portion of the spectrum of a solution prepared by extracting a weighed sample of the food product with a preselected amount of a 6M. aqueous solution of guanidine hydrochloride, comparing the result with a standard curve for representative soy materials derived from soy beans containing high proportions (at least 50 percent) of protein wherein maximum fluorescence intensity at about 445 nanometers wavelength is plotted against amount of soy material, then calculating the percentage of soy material in the sample of food product from the amount of soy material found and the weight of the sample.

10 Claims, No Drawings

METHOD OF DETERMINING SOY MATERIAL IN FOODS

The invention described herein may be manufactured, used, and licensed by or for the Government for governmental purposes without the payment to me of any royalty thereon,

BACKGROUND OF THE INVENTION

This invention relates to a method of determining the soy material content of a food product, particularly a food product prepared by blending soy flour, or the like soy protein-containing material, with some other type of food material, such as ground beef.

Soy protein-containing materials are being used in an increasing number of instances in the food industry for blending with other food materials for a variety of reasons. In some instances the use of a certain percentage of soy flour or other soy protein-containing material in conjunction with a more expensive basic food material, such as ground beef, permits the production of an acceptable but less expensive product than the usual product made without the admixture of the soy material. In other instances use of the soy material in conjunction with various food materials from animal sources results in marked reduction in cholesterol-producing substances in the diet, which may be highly desirable in the cases of persons affected by cardiac problems or concerned about the possibilities of developing cardiac problems. There has, therefore, been a long-standing problem of determining the relative percentages of soy material and the other materials usually present in food products with which soy material is now being blended. This is particularly important for consumers and for governmental agencies who have the responsibility of inspecting food products and insuring that the public is fairly treated in the market place, that blends of soy material with other food products are being priced fairly relative to the concentrations of soy materials in food blends.

It is therefore, an object of the invention to provide a method of determining the amount of soy material in a food product.

Other objects and advantages will become apparent from the following description of the invention.

SUMMARY OF THE INVENTION

A method of determining the amount of soy material in a food product wherein the intensity of the fluorescence of an aqueous guanidine hydrochloride solution of the fluorophore present in a mixture containing soy material is directly proportional to the amount of soy material therein. The fluorescence intensity is measured at about 445 nanometers wavelength, the wavelength of maximum fluorescence intensity of the fluorophore, the constituent responsible for fluorescence of soy material, when a solution as described is excited with ultraviolet radiation of a wavelength of substantially 360 nanometers. With the assistance of a standard table or curve obtained with various representative soy materials which contain high proportions of soy protein in the samples thereof used for obtaining the standard table or curve, the percentage of soy material in the sample of food product is readily calculated.

DESCRIPTION OF THE PREFERRED EMBODIMENT

The method of the invention depends on the fact that the relative intensity of the fluorescence of a solution prepared by extracting a soy material with preferably, a 6M guanidine hydrochloride aqueous solution of a preselected volume, as described at a wavelength of about 445 nanometers (the wavelength at which fluorescence reaches the maximum intensity) when excitation of the solution is carried out using ultraviolet light of a wavelength of 360 nanometers, bears a substantially straight line relationship to the amount of soy material present. Thus it is possible to establish a table of relative values or to plot a curve of relative values of relative intensity of fluorescence versus concentration or amount of soy material, using plane Cartesian coordinates, and to interpolate from the table or the curve and thereby ascertain the amount of soy material present in a sample of food material. Having determined the amount of soy material in a sample of the food material of a given weight, it is a relatively simple matter to calculate the percentage of soy material in the food material using equation (1):

$$\text{Percent soy material in sample} = W_e/W_s \times 100 \qquad (1)$$

wherein $W_e$ = weight equivalent of soy material in the food mixture corresponding to the maximum fluorescence intensity established in a standard table or curve and $W_s$ = weight of the sample of the mixture of food material containing the soy material.

To establish the above-mentioned standard table or standard curve, solutions prepared from samples of representative soy materials having high protein contents (at least 50 percent by weight) of different weights over a range which it is desired to bracket are made up in 6M. guanidine hydrochloride aqueous solution by weighing each sample of the representative soy material into a 5 ml flask, stirring for 20 minutes on a magnetic stirrer-hot plate at 25° C, then filtering each solution separately through a Millipore membrane filter into a vial to remove the insoluble portion of the sample, thereafter exposing an aliquot portion of each solution in a spectrophotofluorometer to excitation radiation in the ultraviolet region at a wavelength of 360 nanometers, and measuring the emission intensities at wavelengths from 340 to 560 nanometers or at the wavelength where fluorescence intensity reaches a maximum. The fluorescence intensity generally reaches a maximum at about 445 nanometers wavelength, although the wavelength at which maximum fluorescence intensity occurs may be from about 440 to about 450 nanometers. There will, of course, be a maximum fluorescence intensity for each separate solution of soy material in 6M guanidine hydrochloride aqueous solution, as shown in Table 1, which covers the amounts of fluorophore-containing material extracted from representative soy materials over a range of from about 2 to 25 mg dissolved in 5 ml of the guanidine hydrochloride solution. The sources of the representative soy materials were soy flour (either defatted standard soy flour, or soy flours containing 4% fat or 14% fat), five textured vegetable proteins (TVP) derived from soy, and three isolated soy proteins (ISP), all of which contain at least 50 percent protein. Three aliquot portions of each sample were measured and the three values for the maximum or relative fluorescence intensity were averaged. Also the mean value of the relative intensity values for all of the samples for each given weight was calculated, and the standard deviations and coefficients of variation were calculated.

obtained, since the weight of soy material is directly proportional to the maximum fluorescence intensity. The percentage of soy material in the sample is readily calculated using equation (1) given above. Using this procedure, various weights of a number of blends of soy material with other food materials were measured for maximum fluorescence intensity (Int.) and the soy contents of the samples and the percentages of soy material in the samples were determined. These are given in Table 2.

TABLE 1

Relative Fluorescence Intensity of Representative Soy Materials

| | 2 mg [a]rel. int. 1 2 3 | Av. | 5 mg. rel. int. 1 2 3 | Av | 10 mg. rel. int. 1 2 3 | Av. | 25 mg. rel. int. 1 2 3 | Av. |
|---|---|---|---|---|---|---|---|---|
| Standard Soy Flour (defatted) | 7 6 8 | 7.0 | 16 17 17 | 16.7 | 33 34 34 | 33.7 | 83 82 84 | 83.0 |
| TVP 1 | 6 8 7 | 7.0 | 17 16 18 | 17.0 | 34 34 34 | 34.0 | 84 83 82 | 83.0 |
| TVP 2 | 7 7 6 | 6.7 | 16 17 17 | 16.7 | 33 34 36 | 34.3 | 83 83 84 | 83.3 |
| TVP 3 | 6 8 7 | 7.0 | 16 18 17 | 17.0 | 35 34 34 | 34.3 | 81 83 83 | 82.3 |
| TVP 4 | 7 7 8 | 7.3 | 17 17 16 | 16.7 | 33 33 34 | 33.3 | 83 83 83 | 83.0 |
| TVP 5 | 7 6 7 | 6.7 | 18 16 17 | 17.0 | 35 35 33 | 34.3 | 82 84 83 | 83.0 |
| ISP 1 | 7 7 7 | 7.0 | 17 17 17 | 17.0 | 34 33 35 | 34.0 | 82 84 82 | 82.7 |
| ISP 2 | 7 8 7 | 7.3 | 17 18 17 | 17.3 | 36 35 33 | 34.7 | 83 83 82 | 82.7 |
| ISP 3 | 8 7 7 | 7.3 | 18 17 17 | 17.3 | 34 36 33 | 34.3 | 81 83 82 | 82.0 |
| Soy Flour 4% Fat | 7 7 8 | 7.3 | 17 18 17 | 17.3 | 33 35 34 | 34.0 | 83 84 81 | 82.7 |
| Soy Flour 14% Fat | 7 9 7 | 7.7 | 18 17 18 | 17.7 | 35 34 35 | 34.7 | 83 84 84 | 83.7 |

[a]1-3 = replicate measurements

| | | | | |
|---|---|---|---|---|
| Mean | 7.1 | 17.1 | 34.2 | 82.9 |
| Std dev. | 0.03 | 0.03 | 0.04 | 0.04 |
| Coeff. of var. (%) | 0.42 | 0.18 | 0.12 | 0.05 |

TABLE 2

Determination of Soy Material Content in Ground Beef and Other Food Blends

| | | Wt. of Sample | | | | | | | | |
|---|---|---|---|---|---|---|---|---|---|---|
| | | 20 mg | | | 35 mg | | | 70 mg | | |
| Sample Ground beef blends | | Rel. Int[a] | Soy Material Cont. (mg) | % Soy Material | Rel. Int[a] | Soy Material Cont. (mg) | % Soy Material | Rel. Int[a] | Soy Material Cont. (mg) | % Soy Material |
| Commercial | 1 | 14.0 | 4.5 | 22.5 | 23.3 | 7.5 | 21.4 | 50.3 | 15.0 | 21.4 |
| | 2 | 15.7 | 5.0 | 25.0 | 28.3 | 8.5 | 24.3 | 63.0 | 18.0 | 25.7 |
| Supermarket | 1 | 9.3 | 3.0 | 15.0 | 16.7 | 5.0 | 14.2 | 35.7 | 10.5 | 15.0 |
| | 2 | 8.0 | 2.5 | 12.5 | 15.3 | 4.5 | 12.9 | 28.0 | 8.5 | 12.1 |
| | 3 | 12.7 | 4.0 | 20.0 | 23.7 | 7.0 | 20.0 | 47.3 | 14.0 | 20.0 |
| | 4 | 10.0 | 3.5 | 17.5 | 20.0 | 6.0 | 17.1 | 42.3 | 12.5 | 17.9 |
| Dairy Whey-Soy | 1 | 20.3 | 7.0 | 35.0 | 41.0 | 12.5 | 35.7 | 82.0 | 24.5 | 35.0 |
| | 2 | 15.7 | 4.8 | 24.0 | 28.3 | 8.5 | 24.3 | 58.3 | 17.5 | 25.0 |
| Wheat Flour-Soy | 1 | 5.0 | 1.6 | 8.0 | 8.7 | 2.8 | 8.0 | 19.3 | 5.5 | 7.9 |
| | 2 | 7.3 | 2.0 | 10.0 | 10.0 | 3.5 | 10.0 | 24.3 | 7.0 | 10.0 |

[a] = Average of 3 determinations

Then to determine the percentage of soy material in a blend of a soy protein-containing material with a given type of food, such as ground beef, dairy whey, or wheat flour, a sample of the blend having a weight which contains soy material falling within the range of the standard table or standard curve is placed in a 5 ml flask to which 6M. guanidine hydrochloride aqueous solution is added, bringing it up to the 5 ml mark. The solution is stirred for 20 minutes at 25° C as in the case of the standard samples, then filtered through a Millipore membrane filter into a vial to remove the insoluble portion of the sample. As with the standard solutions, three aliquot portions are measured for fluorescence intensity in the same manner as described above for the standard samples and the three fluorescence intensity maximum values at 445 nanometers are averaged. By interpolating from the standard table described above or from a standard curve plotted in a plane Cartesian coordinate system, one can read off the standard curve or approximate from the table the weight of soy material which corresponds to or is the equivalent of the average maximum intensity value It will be apparent from the results given in Table 1 that there is an approximately straight line relationship between the maximum fluorescence intensity (designated relative intensity) and the weight of the sample of representative soy materials containing at least 50 percent by weight soy protein. If desired, the mean values for relative intensity may be plotted as ordinate values and the weights of the samples may be plotted as abscissa values in a plane Cartesian coordinate system, which produces a substantially straight line standard curve. From this straight line relation it is easy to determine by interpolation the weight of soy material corresponding to a given maximum fluorescence intensity. Then knowing the weight of soy material in a given sample of food product containing added soy material, it becomes a relatively simple matter to calculate the percentage of soy material in the food product by means of equation (1) given above. Thus, the relative intensity values in Table 2 permit determination by interpolation from the standard curve the weight of soy material in each sample. Insertion of each of these values and the weight of the sample in Equation (1) results in the values for % Soy Material in the various food blends containing soy material shown in Table 2.

Wherever the term "fluorophore" is used in the specification or claims, it is to be understood that this refers to the constituent of the soy material which is responsible for the fluorescence thereof.

Although the invention has been described in terms of using preferably 6M. guanidine hydrochloride in aqueous solution to dissolve the fluorophore which is present in soy materials, other solvents may be employed. For example, other concentrations of guanidine hydrochloride in aqueous solution may be used, although the best results have been obtained with 6M. guanidine hydrochloride in aqueous solution because this solution is so effective for denaturing the protein in soy material so that the fluorophore is made more available to be dissolved in the aqueous solution. However, 8M. urea hydrochloride together with 0.3% sodium dodecyl sulfate may also be used for this purpose even though the high concentration of the urea hydrochloride and the presence of the sodium dodecyl sulfate contribute to the relative fluorescence intensity of the solution of soy material and a correction must, therefore, be made to compensate for this.

The present invention provides the distinct advantage that it is no longer necessary to take on faith a statement by a purveyor of food products that a blend of ground beef contains no more than a certain percentage of added soy material or that other blends of primary food ingredients with soy flour, textured vegetable protein, isolated soy protein or the like sources of soy material have no more therein than a certain stated percentage. These products are as a result of the invention subject to ready analysis for soy material content, particularly by organizations which buy large quantities of such blends and by governmental agencies, both Federal and state, which regularly inspect food products on the open market.

I wish it to be understood that I do not desire to be limited to the exact details described, for obvious modifications will occur to a person skilled in the art.

I claim:

1. A method of determining the amount of soy material in a food product which comprises the steps of, (a) dissolving substantially all of the fluorophore-containing component present in said soy material in a sample of said food product of a selected weight in a preselected volume of a solvent for said fluorophore-containing component, (b) separating the insoluble portion of said sample of food product from the solution of said fluorophore-containing component, (c) exposing said solution of fluorophore-containing component to ultraviolet radiation at about 360 nanometers wavelength, (d) determining the maximum fluorescence intensity of said solution of fluorophore-containing component at the wavelength at which maximum fluorescence intensity occurs, and (e) comparing said maximum fluorescence intensity with a standard curve for fluorescence intensity versus quanity of soy material obtained using representative soy materials to determine the quantity of soy material in said sample.

2. A method according to claim 1, wherein said solvent is an aqueous solution of guanidine hydrochloride.

3. A method according to claim 2, wherein said aqueous solution of guanidine hydrochloride has a concentration of about 6 mols of guanidine hydrochloride per liter of aqueous solution.

4. A method according to claim 1, wherein said wavelength at which said maximum intensity occurs is from about 440 to about 450 nanometers.

5. A method according to claim 4, wherein said wavelength at which said maximum fluorescence occurs is about 445 nanometers.

6. A method according to claim 3, wherein said wavelength at which said maximum fluorescence intensity occurs is about 445 nanometers.

7. A method according to claim 1, wherein said representative soy materials comprise at least about 50 percent by weight soy protein.

8. A method according to claim 1, wherein the additional step of calculating the percentage of soy material present in said sample of food product is carried out after completing step (e) by applying the equation:

Percent soy material in sample = $W_e/W_s \times 100$ wherein $W_e$ = weight equivalent of soy material in the food mixture corresponding to the maximum fluorescence intensity established in a standard table or standard curve and $W_s$ = weight of the sample of the mixture of food material containing the soy material.

9. A method according to claim 1, wherein said solvent is an aqueous solution of urea hydrochloride and sodium dodecyl sulfate.

10. A method according to claim 9, wherein said aqueous solution of urea hydrochloride and sodium dodecyl sulfate has a concentration of about 8 mols of urea hydrochloride per liter of aqueous solution and about 0.3% sodium dodecyl sulfate.

* * * * *